United States Patent

Fujibayashi et al.

[11] Patent Number: 5,904,915
[45] Date of Patent: May 18, 1999

[54] METHOD OF DIAGNOSING PATHOLOGICAL STATE OF TUMOR CELLS USING A DIAGNOSTIC AGENT FOR GLYCOMETABOLIC FUNCTION

[75] Inventors: Yasuhisa Fujibayashi, Kyoto-fu; Atsuo Waki, Fukui-ken; Akira Yokoyama, Shiga-ken, all of Japan

[73] Assignee: Nihon Medi-Physics Co., Ltd., Hyogo-ken, Japan

[21] Appl. No.: 08/825,049

[22] Filed: Mar. 27, 1997

[30] Foreign Application Priority Data

Mar. 28, 1996 [JP] Japan ..................... 8-099252

[51] Int. Cl.⁶ ............... A61K 51/06; A61K 51/04; A61N 57/00; G01N 33/00
[52] U.S. Cl. ............... 424/1.73; 424/1.85; 424/1.89; 514/23; 514/62; 436/14; 436/95
[58] Field of Search ................. 424/1.73, 1.65, 424/1.85, 1.89; 514/23, 62, 724, 727, 738; 536/18.7, 55.2; 435/14, 200; 436/95, 14; 600/365

[56] References Cited

U.S. PATENT DOCUMENTS 5,034,212 7/1991 Yokoyama et al. ............... 424/1.73

FOREIGN PATENT DOCUMENTS 0413145 2/1991 European Pat. Off. .
0676205 10/1995 European Pat. Off. .
2817336 10/1979 Germany .

OTHER PUBLICATIONS

Hamacher et al., "Efficient Stereospecific Synthesis of No–Carrier–Added 2–[¹⁸F]–Flouro–2–Deoxy–D–Glucose . . . substitution", *The Journal of Nuclear Medicine*, vol. 27, No. 2, Feb. 1986, pp. 235–238.

Magata et al., "Development of a Novel Radioiodinated Glucose Derivative with Interaction to Hexokinase", *Journal of Labelled Compounds and Radiopharmaceuticals*, vol. 31, No. 4, 1992, pp. 317–328.

C. Shiue et al., "A New Improved Synthesis of 2–Deoxy–2–[¹⁸F]Fluoro–D–Glucose from ¹⁸F–Labeled Acetyl Hypofluorite", *The Journal of Nuclear Medicine*, vol. 23, No. 10, Oct. 1982, pp. 899–903.

G. Kloster et al., "D–Glucose Derivatives Labelled with $^{75,77}$Br and $^{123}$I", *Journal of Labelled Compounds and Radiopharmaceuticals*, vol. 20, No. 3, 1983, pp. 391–415.

B. Connolly et al., "Affinity Labelling of the Rat Muscle Hexokinase Type II", *Biochemical Society Transactions*, vol. 6, No. 3, 1978, pp. 586–587.

Patent Abstracts of Japan, vol. 096, No. 002, Feb. 29, 1996.

*Primary Examiner*—José G. Dees
*Assistant Examiner*—Michael G. Hartley
*Attorney, Agent, or Firm*—Sughrue, Mion, Zinn, Macpeak & Seas, PLLC

[57] ABSTRACT

A diagnostic agent for glycometabolic function comprising a glucose derivative of the formula (I):

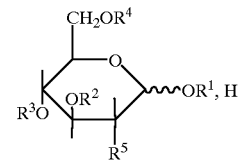

wherein $R^1$, $R^2$, $R^3$ and $R^4$ are the same or different and each represents hydrogen or acyl having 2 to 8 carbon atoms, with the proviso that at least one of $R^1$, $R^2$, $R^3$ and $R^4$ is acyl and $R^5$ represents X or —NHCOR⁶X wherein X is a radioisotope of halogen and $R^6$ is arylene or alkylene having 1 to 3 carbon atoms.

5 Claims, 7 Drawing Sheets

A: FDG + glucose
(concentration of glucose in the incubation medium: 11.2mM)
B: FDG + glucose
(concentration of glucose in the incubation medium: 22.4mM)
C: AFDG + glucose
(concentration of glucose in the incubation medium: 11.2mM)
D: AFDG + glucose
(concentration of glucose in the incubation medium: 22.4mM)

A : FDG
B : FDG - 6P
C : AFDG
D : FDG - 6P

METHOD OF DIAGNOSING PATHOLOGICAL STATE OF TUMOR CELLS USING A DIAGNOSTIC AGENT FOR GLYCOMETABOLIC FUNCTION

BACKGROUND OF THE INVENTION

1. Field of the Invention

The present invention relates to a diagnostic agent for glycometabolic function comprising a glucose derivative as an active ingredient. In particular, the present invention relates to a diagnostic agent which is useful for indicating the glycometabolic function in a tumor site in various tumor diseases.

2. Background Information

Of energy sources necessary for activity of humans, in particular, glucose is taken up from the blood into cells through the glucose transporter (hereinafter, referred to as GLUT), enters into the metabolic pathway after being converted to glucose-6-phosphate by the action of hexokinase and forms energy-rich phosphate compounds such as adenosine triphosphate (ATP), which are utilized as energy sources in living organisms. Particularly, glucose is the unique and important energy source in brain. It is accepted that the change of GLUT is minor and conversion to glucose-6-phosphate from glucose by hexokinase is the rate-determining step in the glycometabolism in brain tissue. Therefore, diagnosis of glucose metabolism in brain by positron emission tomography (PET) has been conducted using radioactive fluorodeoxyglucose which acts in a manner similar to that of glucose in passage through the blood-brain barrier and in metabolism towards 6-phosphate compounds by the action of hexokinase.

It has been known that, also in cells having abnormality such as tumor cells, necessary energies are provided by glucose and the blood glucose level has a great influence on the glycometabolism. Since, however, changes in both the membrane transport and phosphorylation are more complicated, qualitative diagnosis of the pathological state of tumor by radioactive fluorodeoxyglucose has been considered difficult in spite of the fact that there have been many articles showing positive correlation between growth rate of tumors which is an indicator of malignancy of tumor and hexokinase activity.

Figure 8:
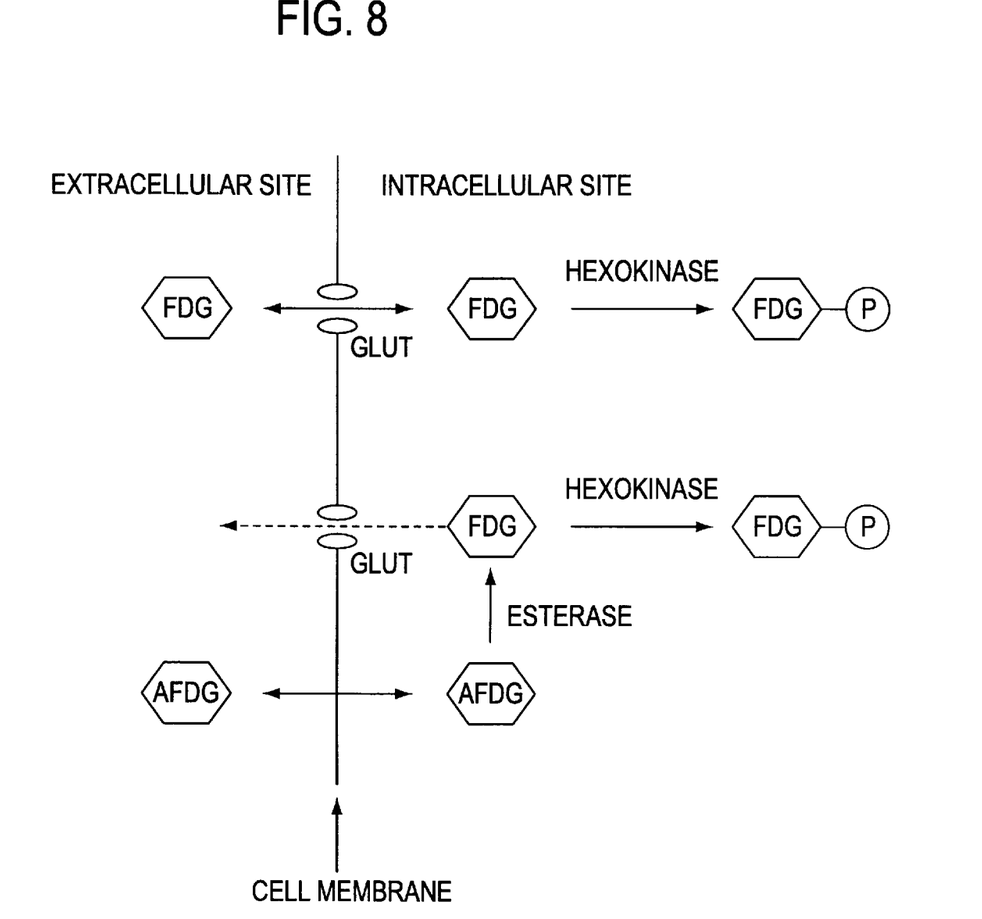
FIG. 8 shows the uptake and subsequent behavior in metabolism of FDG and AFDG in cells.

It has been well known that 2-[F-18]fluorodeoxyglucose (hereinafter, referred to as FDG) acts in a manner similar to that of glucose in the glycometabolic pathway, and it enters into cells with the aid of GLUT and is phosphorylated by the action of hexokinase. It is expected, on the other hand, that 1,3,4,6-tetra-O-acetyl-2-[F-18]fluorodeoxyglucose (hereinafter, referred to as AFDG), an acetylation product of FDG, is taken up into cells without the aid of GLUT, hydrolyzed by an esterase to form FDG, which is phosphorylated by hexokinase similarly to FDG taken up into cells with the aid of GLUT. The behavior of them can be schematically shown in FIG. 8. As the result of an extensive study about the metabolic behavior of AFDG and FDG in tumor cells, the present inventors have discovered that a change in hexokinase activity can be detected on the basis of the fact that AFDG is taken up into cells without the aid of GLUT, quickly hydrolyzed by an esterase to form FDG, which is phosphorylated by hexokinase irrespective of extracellular glucose concentration, and successfully completed the present invention.

Thus, the purpose of the present invention is to provide a diagnostic agent useful for diagnosis of glycometabolic function using the compound which is taken up into cells without the aid of GLUT, immediately acts as a substrate for hexokinase and is metabolized in a manner similar to that of glucose and is able to be an indicator for hexokinase activity in the metabolism, particularly to provide a diagnostic agent therefor which is useful for indicating the glycometabolic function in a tumor site in various tumor diseases.

SUMMARY OF THE INVENTION

In one aspect, the present invention provides a diagnostic agent for glycometabolic function comprising a glucose derivative of formula I:

(I)

wherein $R^1$, $R^2$, $R^3$ and $R^4$ are the same or different and each represent hydrogen or acyl having 2 to 8 carbon atoms, with the proviso that at least one of $R^1$, $R^2$, $R^3$ and $R^4$ is acyl and $R^5$ represents X or —$NHCOR^6X$ wherein X is a radioisotope of halogen and $R^6$ is arylene or alkylene having 1 to 3 carbon atoms.

In another aspect, the present invention provides use of the glucose derivative represented by the above formula (I) as a diagnostic agent for indicating glycometabolic function and the pathological state of tumor characterized by a variable hexokinase activity on said glucose derivative as an indicator.

DETAILED DESCRIPTION OF THE INVENTION

The glucose derivative used in the present invention is taken up into cells without the aid of GLUT and acts as a substrate for hexokinase showing a behavior in metabolism similar to that of glucose. Therefore, the hexokinase activity can be estimated by measuring the amount of the phosphorylated glucose derivative of the produced metabolites and thus glycometabolic function and the pathological state of tumor such as malignancy or growth rate of tumor can be indicated using the hexokinase activity as an indicator.

Figure 1:
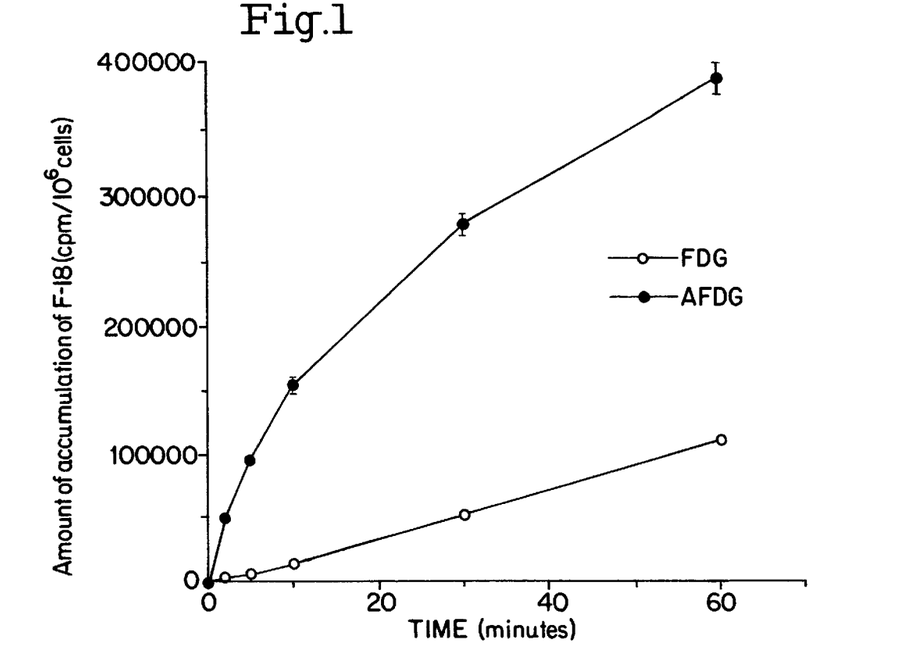
FIG. 1 shows the accumulation in time course of FDG and AFDG in LS180 cells.

Accumulation of FDG and that of AFDG in LS180 tumor cells are compared in FIG. 1. While FDG accumulated and increased almost linearly, AFDG accumulated rapidly in cells in a nonlinear manner and showed accumulation more than three times higher than that of FDG after 60 minutes. Moreover, in an experiment for the effect of temperature on accumulation of AFDG in cells (FIG. 2), the accumulation of AFDG at low temperature, 4° C. was one fourth of that at 37° C., indicating that the accumulation of AFDG depends on the temperature. Furthermore, in an experiment for change in intracellular accumulation of AFDG with the change of administered dose of AFDG (FIG. 3), the accumulation of AFDG in tumor cells increased with the increase of the dose of AFDG. Should the hydrolysis of AFDG by esterase be the rate-determining step in metabolism, the rate of accumulation would be dropped depending on the administered dose of AFDG at the stage. In fact, such result could not be seen and thus it is clear that the hydrolysis of AFDG by esterase does not limit the accumulation of AFDG in tumor cells.

Figure 4:
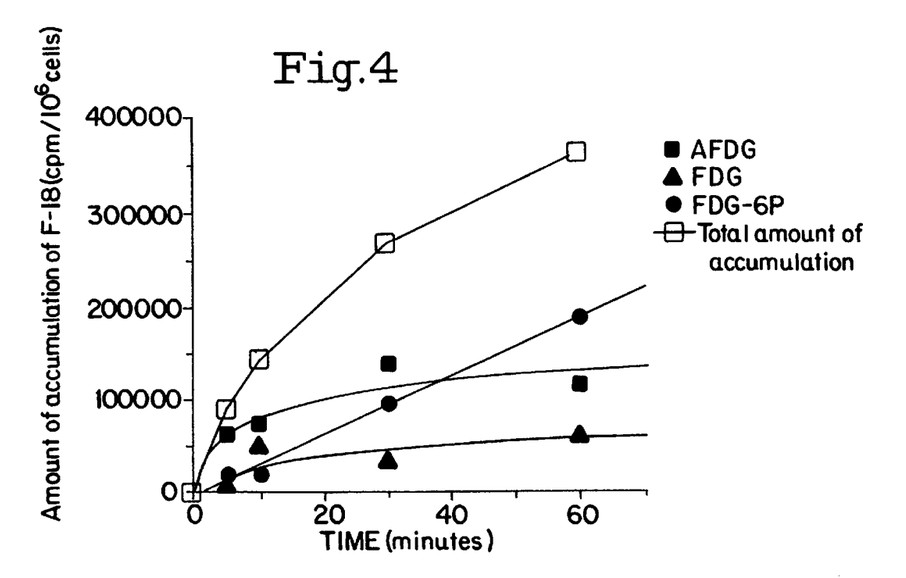
FIG. 4 shows the relation between results of analysis of AFDG metabolites in LS180 cells and time course.

Despite the fact that AFDG is stable in the extracellular medium, it is quickly hydrolyzed by esterase to FDG once it is taken up into cells. This fact was confirmed by an experiment on metabolism of AFDG as shown in FIG. 4. While FDG as a hydrolytic product of AFDG and FDG 6-phosphate (hereinafter, referred to as FDG-6P) as a metabolic product of FDG were substantially absent 5 minutes after the uptake of AFDG into cells, accumulation of FDG-6P increased linearly with passage of time but accumulation of AFDG and that of FDG followed a constant course.

Figure 5:
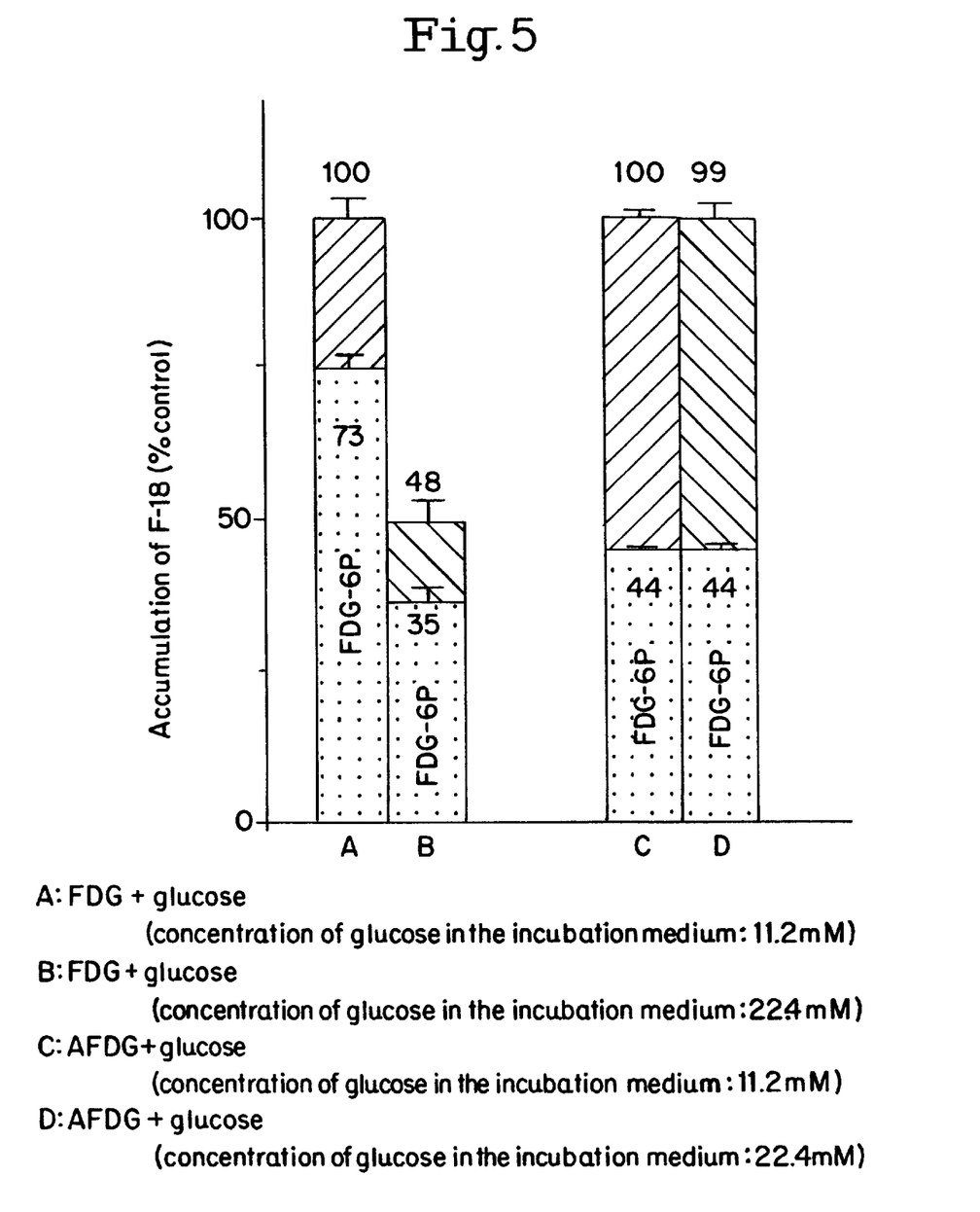
FIG. 5 shows the effect of glucose concentration in medium on accumulation and metabolism of FDG and AFDG in LS180 cells.

The results of experiment in which whether or not the accumulation of FDG or AFDG in tumor cells is affected by glucose concentration in extracellular medium are shown in FIG. 5. In the case of FDG administration, when the glucose concentration in the medium was doubled, the accumulation of FDG in cells decreased and simultaneously the production of FDG-6P also decreased. On the other hand, in the case of AFDG administration, the accumulation of FDG (hydrolysate of AFDG) in cells and production of FDG-6P did not change even if the glucose concentration in the medium was doubled. This means that FDG produced by hydrolysis of AFDG is phosphorylated by hexokinase irrespective of the glucose concentration in medium.

From the facts that the amount of administration of AFDG is extremely little (5 $\mu$Ci=10 $\mu$M) and that FDG produced from administered AFDG stays within cells (FIG. 4), it can be clearly understood that the rate of hydrolysis of AFDG taken up into cells is not the rate-determining step for the metabolism of AFDG. Since the uptake and excretion of FDG into and from cells are carried out with the aid of GLUT, FDG produced from AFDG flows out to the extracellular medium but does not enter again into the cells under conditions in which intracellular concentration of FDG always higher. Therefore, it is understood that the intracellular accumulation of AFDG depends on the hexokinase activity.

Since the accumulation of glucose was not inhibited when AFDG was administered, the administration of AFDG in an amount used in this experiment does not affect the glycometabolism. From the facts that the accumulation of AFDG into LS180 cells 60 minutes after administration is about 3.3 times higher than that of FDG (FIG. 1), that the radioactivity detected from FDG-6P produced for 60 minutes from the administration of AFDG is about 50% of the total intracellular radioactivity and the production of FDG-6P in case of administration of AFDG is considerably higher (1.63 times) than that in case of administration of FDG (FIG. 4 and FIG. 9) and that no change was observed in the amount of FDG-6P, the metabolite, as seen in the experiment for studying effect of the glucose concentration on the accumulation of AFDG (FIG. 5), it can be understood that the amount of produced FDG-6P depends on the difference of uptake route before the phosphorylation step of FDG, i.e. whether or not the uptake is made with the aid of GLUT.

In an experiment for studying change in the accumulation of FDG and AFDG under conditions in which hexokinase was inhibited using iodoacetate, an inhibitor for hexokinase (FIG. 6), the accumulation of AFDG was remarkably decreased indicating that the intracellular accumulation of AFDG was remarkably affected by the decrease in hexokinase activity. On the other hand, from the fact that the accumulation of FDG after administration of FDG was also remarkably decreased, it can be understood that the hexokinase activity was remarkably decreased by IAA even to a level below FDG uptake capacity of GLUT. This indicates that the rate-determining step of accumulation and metabolism of FDG was changed from transport through GLUT to hexokinase activity.

While it is known that 2,4-dinitrophenol, an uncoupling agent for mitochondrion, causes expression of GLUT on cell membrane to normal cells by a transient decrease of intracellular ATP as a trigger, it has not been confirmed that it has a similar effect on tumor cells. Therefore, transport of [H-3]-3-O-methylglucose in the DNP-treated tumor cells was studied for the case in which GLUT was inhibited by cytocharasin B and for the case in which it was not inhibited, respectively. [H-3]-3-O-methylglucose is a D-glucose derivative which is not subjected to metabolism such as phosphorylation after take up into cells and therefore can suitably be used in an experiment for studying transport ability of GLUT. In the case of DNP treatment, accumulation of [H-3]-3-O-methylglucose was increased by about 70% as compared with the case of no treatment (Table 1), and therefore it was considered that the amount of GLUT expressed on the cell membrane was increased by 70% with the treatment by DNP. The increase in amount was by far smaller than the increase described for normal cells. This is due to the fact that the amount of GLUT expressed on the tumor cell membrane is by far greater than the amount for normal cells.

Figure 7:
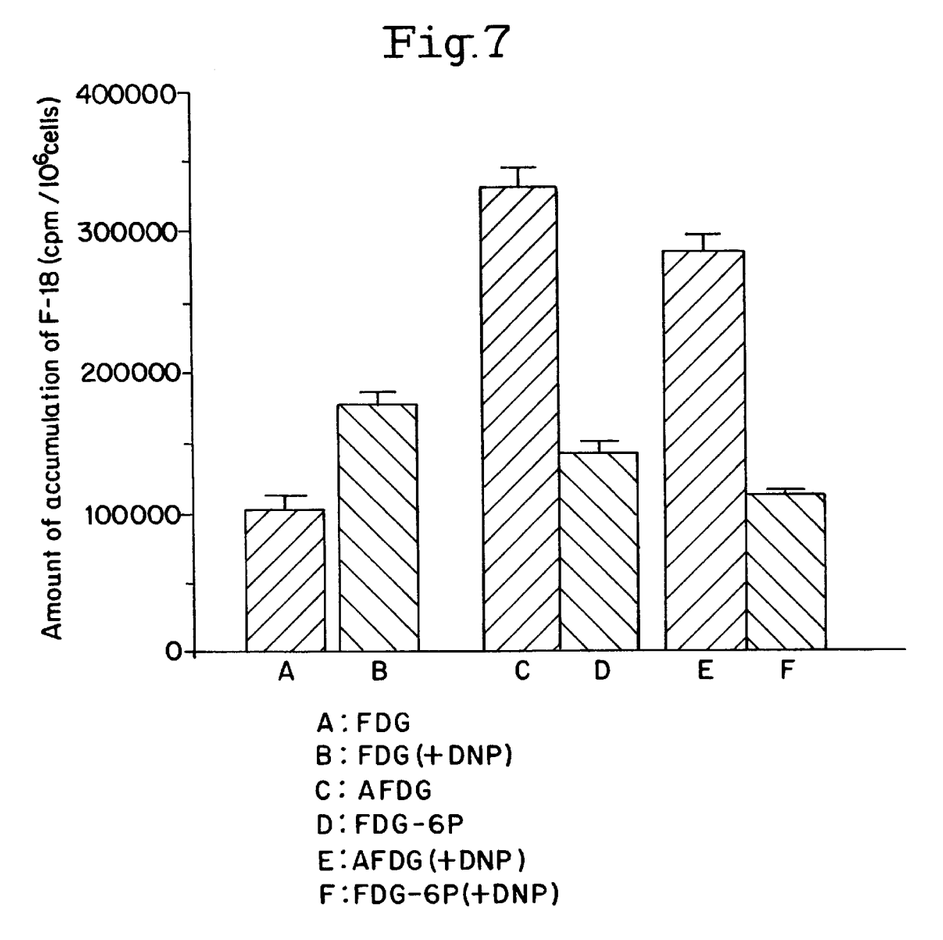
FIG. 7 shows the effect of 2,4-dinitrophenol (hereinafter referred to as DNP) on accumulation and metabolism of FDG and AFDG in LS180 cells.

When the expression of GLUT on tumor cell membrane was increased, the uptake of FDG was increased by about 80% but production of FDG-6P from AFDG was decreased by about 20% (FIG. 7). From this result, it can be considered that, in tumor cells, FDG derived from AFDG competes against glucose accumulated as the result of activated uptake of glucose due to the increase of GLUT expression, which results in decrease of FDG-6P produced from AFDG.

As described above, it has been proved that the rate-determining step in the glucose metabolism depends either on the expression amount of GLUT or hexokinase activity in cell in question and shows a change between the transport step through GLUT and the metabolic step by hexokinase, depending on the pathological state of the cell. More precisely, it is understood that, in tumor cells, the accumulation of FDG on administration of FDG does not reflect phosphorylation ability itself by hexokinase but is limited by the uptake through GLUT and that the rate-determining step in the glycolytic pathway is the transport of FDG through GLUT. From these discussion, it can be concluded that, while FDG is taken up into cells with the aid of GLUT and metabolized by hexokinase to FDG-6P, AFDG is taken up into cells without the aid of GLUT but the uptake of it is made by simple diffusion and metabolism to FDG-6P depending on hexokinase activity. In summary, it is concluded that AFDG has the following intracellular accumulation mechanism:

i) It is taken up by simple diffusion and is not subjected to the aid of GLUT.

ii) The acetyl group of AFDG taken up into cells is quickly hydrolyzed to form FDG and the velocity of hydrolysis is greater then that of phosphorylation of FDG.

iii) The produced FDG is subjected to phosphorylation by hexokinase.

iv) After 60 minutes, about 50% of the sum of AFDG, FDG and FDG-6P is the end metabolite FDG-6P.

As described above, AFDG is taken up into cells irrespective of the expression amount of GLUT and quickly hydrolyzed to FDG, which acts as a substrate for hexokinase and is subjected to glycometabolism having a rate-determining step of phosphorylation by hexokinase. Accordingly, since AFDG is not affected by GLUT even in complicated the pathological state in which the rate-determining step in glycometabolism changes between the transport through GLUT and phosphorylation by hexokinase, it can be utilized for a diagnostic composition which is very effective for indicating the pathological state of tumor of human subject using PET.

The glucose derivative used in the present invention is a compound which is taken up into cells irrespective of the expression amount of GLUT. In the formula (I), $R^1$, $R^2$, $R^3$ and $R^4$ are hydrogen or acyl, among which at least one is acyl. Examples of acyl group include acetyl, propionyl, butyryl, benzoyl and the like, among which acetyl is the most suitable. Suitable radioisotopes of halogen include radioisotopes of fluorine, bromine and iodine, among which radioisotopes of fluorine are preferred. The radioisotope of halogen may be directly labeled at the 2-position of the glucose derivative or may be attached through an amide linkage to glucosamine as a glucose derivative. In other words, $R^5$ may be —NHCOR$^6$X. $R^6$ is alkylene or arylene, and alkylene includes methylene, ethylene, trimethylene and arylene includes phenylene.

Specifically, examples of the glucose derivative include 1,3,4,6-tetra-O-acetyl-2-fluorodeoxyglucose, 1,3,4-tri-O-acetyl-2-fluorodeoxyglucose, 1,3,4-tri-O-acetyl-6-O-butyryl-2-fluorodeoxyglucose, 6-O-acetyl-2-fluorodeoxyglucose, 1,3-di-O-acetyl-6-O-butyryl-2-fluorodeoxyglucose, 1-O-benzoyl-2-fluorodeoxyglucose, 3,4,6-tri-O-acetyl-2-fluorodeoxyglucose, 1,3,4,6-tetra-O-acetyl-N-(fluorobenzoyl)-glucosamine, 1,3,4,6-tetra-O-acetyl-N-(fluoroacetyl)-glucosamine, 1,3,4,6-tetra-O-acetyl-N-(fluorobutyryl)-glucosamine, 1,3,4,6-tetra-O-acetyl-2-bromodeoxyglucose, 1,3,4-tri-O-acetyl-2-bromodeoxyglucose, 1,3,4-tri-O-acetyl-6-O-butyryl-2-bromodeoxyglucose, 6-O-acetyl-2-bromodeoxyglucose, 1,3-di-O-acetyl-6-O-butyryl-2-bromodeoxyglucose, 1-O-benzoyl-2-bromodeoxyglucose, 3,4,6-tri-O-acetyl-2-bromodeoxyglucose, 1,3,4,6-tetra-O-acetyl-N (bromobenzoyl)-glucosamine, 1,3,4,6-tetra-O-acetyl-N (bromoacetyl)-glucosamine, 1,3,4,6-tetra-O-acetyl-N-(bromobutyryl)-glucosamine, 1,3,4,6-tetra-O-acetyl-2-iododeoxyglucose, 1,3,4-tri-O-acetyl-2-iododeoxyglucose, 1,3,4-tri-O-acetyl-6-O-butyryl-2-iododeoxyglucose, 6-O-acetyl-2-iododeoxyglucose, 1,3-di-O-acetyl-6-O-butyryl-2-iododeoxyglucose, 1-O-benzoyl-2-iododeoxyglucose, 3,4,6-tri-O-acetyl-2-iododeoxyglucose, 1,3,4,6-tetra-O-acetyl-N-(iodobenzoyl)-glucosamine, 1,3,4,6-tetra-O-acetyl-N-(iodoacetyl)-glucosamine, 1,3,4,6-tetra-O-acetyl-N-(iodobutyryl)-glucosamine and the like and the compound substituted with other radioisotope of halogen. Among them, 1,3,4,6-tetra-O-acetyl-[F-18]fluorodeoxyglucose is preferred.

The glucose derivative according to the present invention may be prepared for a diagnostic agent by mixing with pharmaceutically acceptable additives (or auxiliary or carrier or diluent). Examples of the additives include pharmaceutically acceptable stabilizer such as ascorbic acid or p-aminobenzoic acid, pH adjusting agents such as hydrochloric acid or sodium hydroxide, suitable buffers such as phosphate buffer and isotonicity agents such as physiological saline.

The diagnostic agent for examining glycometabolism according to the present invention may be administered by any conventional parenteral means including intravenous injection or infusion of bolus and the amount of administration is decided considering various conditions such as weight, age and sex of patient and radiation imaging apparatus. In the case of human subject, the amount is usually 37 MBq–555 MBq and preferably 111 MBq–370 MBq.

For glucose or FDG, the rate-determining step in the metabolism shows a change between the transport step through GLUT and the phosphorylation step by hexokinase, depending on the pathological state, because glucose or FDG is taken up into cells with the aid of GLUT and metabolized. On the other hand, the glucose derivatives used in the present invention are taken up without the aid of GLUT and metabolized by hexokinase and therefore are very useful for indicating the pathological state by means of PET.

EXAMPLES

The present invention will now be illustrated in more detail with the following Examples. Also, methods of synthesis and analysis for FDG and AFDG as well as a method of culturing tumor cells used in Examples are described in Reference Examples. Further, an experiment for examining effects of DNP causing expression of GLUT on cell membrane on tumor cells and results are also shown in Reference Example.

Reference Example 1

Syntheses of FDG and AFDG

The syntheses of FDG and AFDG were carried out according to the method described by Hamacher et al (J. Nucl. Med., 27, 235–238, 1986) using a automatic synthesizer (manufactured by NKK corporation). F-18 ions were obtained from [O-18]H$_2$O by the reaction $^{18}$O(p,n)$^{18}$F using a small cyclotron for medical use (manufactured by NKK corporation and a solution containing 26 mg of aminopolyether potassium complex (Kriptofix 2.2.2) in acetonitrile was added thereto and mixed in a reactor. The mixed solution was evaporated to dryness. The acetonitrile solution was added to 20 mg of 1,3,4,6-tetraacetyl-2-O-trifluoromethanesulfonyl-β-D-mannnopyranose (triflate) and the mixture was subjected to substitution reaction for 5 minutes. Upon completion of the reaction, water was added to the mixture and the obtained solution was passed through a Sep-pak C18 column in order to purify the reaction product. A solution containing the reaction product obtained by eluting the Sep-pak C18 column with acetonitrile was evaporated twice to dryness. For the synthesis of AFDG, 2 ml of dimethylsulfoxide (DMSO) was added to the above evaporated reaction product. For the synthesis of FDG, 3 ml of 2N hydrochloric acid was added to the above evaporated reaction product and hydrolysis reaction was carried out at 130° C. for 5 minutes. The synthesis of FDG was completed by passing through a ion retarding resin column, evaporating to dryness and reconstituting a solution with water as the solvent.

Reference Example 2

Analyses of FDG and AFDG

FDG and AFDG were assayed for purity of radioactivity with a high performance liquid radiochromatography using a column for carbohydrate analysis (WATERS, 3.9×300 mm, acetonitrile/water=95/5, flow rate: 2 ml/min). FDG and AFDG had respective peaks at flow volume of approximately 4.1 ml and 2.5 ml.

Reference Example 3

Culture of Tumor Cell

A cell line human colon cancer cell LS180 was cell-cultured in RPM 11640 (GIBCO-BRL) containing 10% fetal bovine serum using a petri dish (diameter; 10 cm).

Reference Example 4

Effect of DNP on Rate of Uptake of 3-OMG

For studying uptake of [H-3]-3-O-methylglucose (3-OMG) into cells excluding nonspecific bonding, usually cytocharasin B is used. After incubating $10^6$ LS180 cells in a medium containing 200 $\mu$M DNP placed in a plate having 24 holes, the medium was changed to a medium containing 5 $\mu$Ci 3-OMG and 200 $\mu$M DMP, respectively, and additionally 50 $\mu$M cytocharasin B or a medium without cytocharasin B and the respective cultures were incubated for 60 seconds. Immediately after, the medium was removed and cells were washed three times with a cold PBS containing 0.1 mM phloretin and lysed with 500 $\mu$l of 0.2 N NaOH solution. After lysis, a 200 $\mu$l portion was used for quantitative determination of proteins and the remaining 300 $\mu$l was mixed with a scintillator and radioactivity was measured by a liquid scintillation counter (LSC 5000, manufactured by Aloka corporation). The taken-up amount of 3-OMG which may be inhibited by cytocharasin B was integrated from the difference in mean values of 10 holes in the plate for 3-OMG uptake without cytocharasin B. The results of the experiment are shown in Table 1.

Also in tumor cells, the expression amount of GLUT was increased and the rate of increase was 1.7 times of that without the DNP treatment.

TABLE 1

| Cytocharasin B | Accumulation of [H-3]3-OMG (dpm/min/100 $\mu$g protein) | |
|---|---|---|
| | Control | DNP treatment |
| Absent | 3235 ± 307 | 4763 ± 669 |
| Present | 1511 ± 231 | 1303 ± 229 |
| Difference | 2014 (1.00) | 3460 (1.71) |

Example 1

Accumulation of FDG and AFDG in Tumor Cell LS180

Experiment 1

LS180 cells were stripped off from the petri dish using trypsin, inoculated on a plate having 24 holes at a concentration of $20\times10^4$ cells/ml and subjected to the uptake experiment after 24 hours. Each 5 $\mu$Ci of FDG and AFDG were added thereto and incubated for 2, 5, 10, 30 and 60 minutes, respectively. Then, the media were removed and cells were washed twice with a phosphate buffered-saline (PBS) and lysed with 50 $\mu$l of 0.2 N NaOH solution. Radioactivity of the lysed solution was measured by an Autowell gamma counter (ARC-2000, manufactured by Aloka corporation). The results are shown in FIG. 1. While FDG accumulated linearly, AFDG accumulated rapidly in cells in a nonlinear manner and showed accumulation more than three times higher than that of FDG after 60 minutes.

Experiment 2

Figure 2:
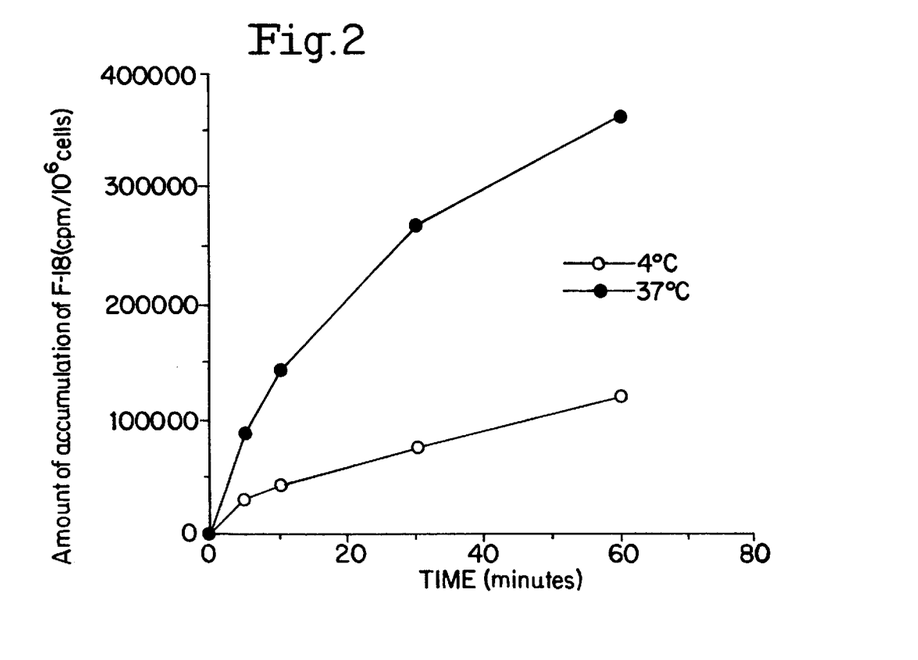
FIG. 2 shows the effect of temperature on accumulation in time course of AFDG in LS180 cells.

In order to study the temperature dependence of intracellular accumulation of AFDG, an uptake experiment was conducted different from Experiment 1. Cells were suspended in a culture medium at a concentration of $1\times10^6$ cells/ml and incubated in portions of 1 ml at 4° C. or 37° C. for 15 minutes. Then, 5 $\mu$Ci of AFDG was added and incubated for 2, 5, 10, 30 and 60 minutes, respectively. At every determined times, cells were centrifuged to make a pellet, which was washed with a cold PBS. After washing twice, the pellet was lysed by 0.2N NaOH solution and assayed for radioactivity. The results are shown in FIG. 2.

The accumulation of AFDG 60 minutes after administration at 4° C. was one fourth of that at 37° C., suggesting that the accumulation of AFDG depends on the temperature.

Experiment 3

Figure 3:
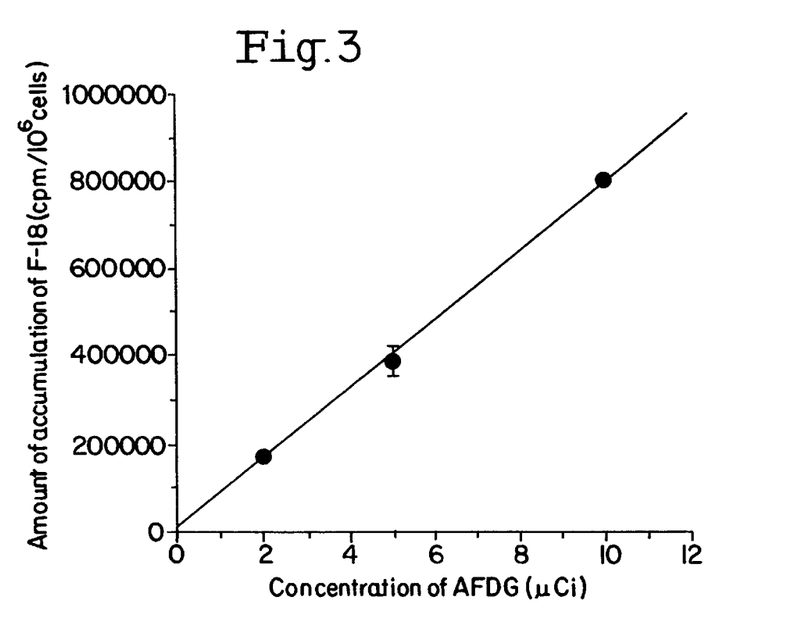
FIG. 3 shows the effect of administered dose of AFDG on accumulation of AFDG in LS180 cells.

In a similar manner, an experiment was conducted to know the effect in intracellular accumulation of AFDG with the change of administered dose of AFDG. The results are shown in FIG. 3. The accumulation of AFDG in tumorcells increased with the increase of the dose of AFDG. From this results, it was revealed that the rate-determining step of metabolism of AFDG was not hydrolysis by esterase.

Example 2

Metabolism of AFDG in LS180 Cells

After carrying out an experiment according to Experiment 1, cells were stripped off from the plate using 100 $\mu$l of 50% ethanol and the solution was centrifuged at 15000 rpm. A 25 $\mu$l aliquot of supernatant was subjected to analysis of metabolites by thin-layer chromatography (TLC). The eluent was acetonitrile/water=95/5, and the carrier was silica gel 60. The plate after development was cut at 5 mm intervals and assayed for radioisotope with a gammer counter. Total radioactivity of respective metabolites were calculated from the ratio of metabolites obtained in TLC. Of the results of experiment, the metabolism of AFDG is shown in FIG. 4. FDG as a hydrolytic product of AFDG and FDG-6P as a metabolic product of FDG were substantially absent in cells 5 minutes after the administration of AFDG. Thereafter, accumulation of FDG-6P increased linearly with passage of time but accumulation of AFDG and that of FDG followed a constant course. This is due to the fact that the metabolism of AFDG to FDG is fast but that of FDG to FDG-6P was slow.

Figure 9:
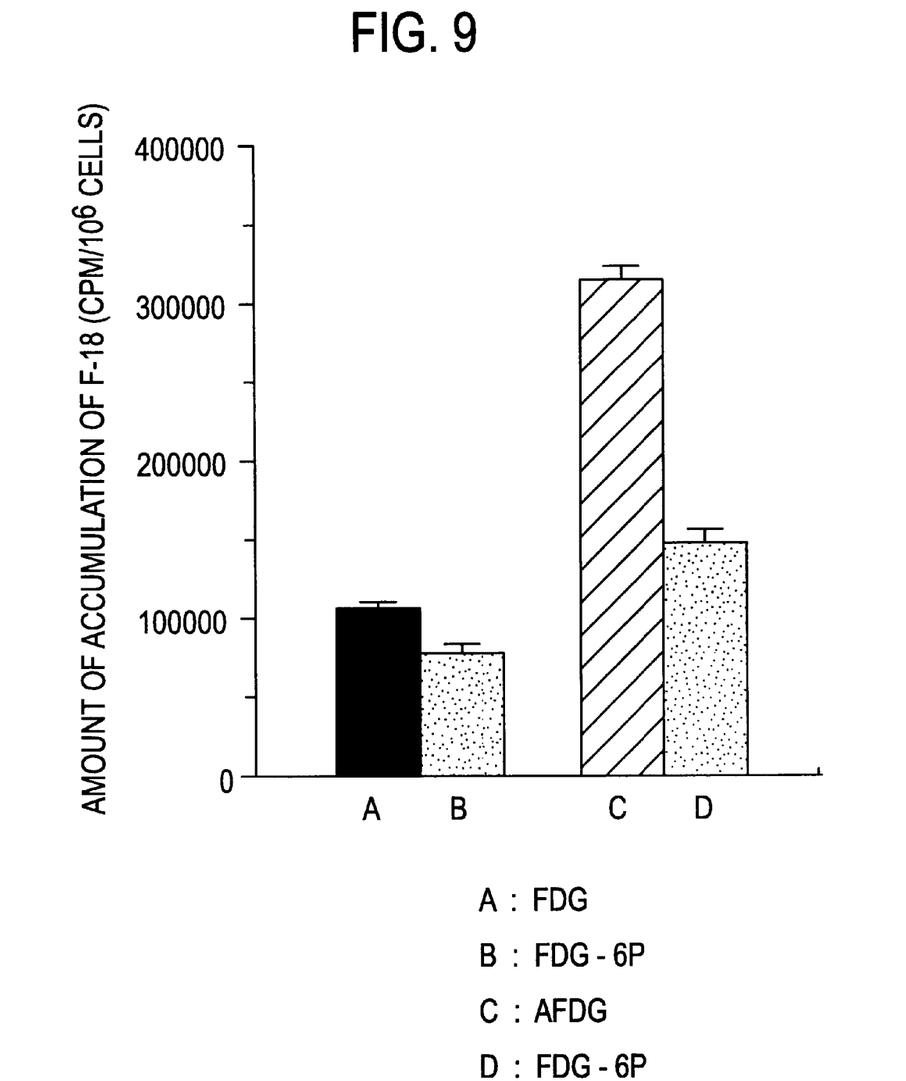
FIG. 9 shows the accumulation of FDG, AFDG and metabolites of FDG and AFDG 60 minutes after administration.

Moreover, in order to compare metabolism of AFDG 60 minutes after administration of AFDG with that of FDG 60 minutes after administration of FDG, same experiment was carried out except that incubation time after administration of AFDG and FDG was 60 minutes. The results are shown in FIG. 9. The amount of the accumulation of AFDG was three times in comparison with that of FDG and the amount of FDG-6P produced from AFDG is considerably higher (1.63 times) than that from FDG. From this result, it can be understood that the route of uptake of AFDG into cell and rate-determining step of metabolism of AFDG are different from those of FDG.

Example 3

Effect of Extracellular Glucose Concentration on Accumulation and Metabolism of FDG and AFDG in LS180 Cells In order to know the effect of the glucose concentration in the medium on the intracellular accumulation of FDG and AFDG, two kinds of culture media having a glucose concentration of 11.2 mM and 22.4 mM, respectively, were prepared. Cells were incubated in the culture media having a glucose concentration of 11.2 mM and 22.4 mM, respectively, with 5 µCi of each of FDG and AFDG for 60 minutes. Then, cells were washed three times with a cold PBS, lysed with 50% ethanol and the lysate was assayed for metabolites. The results are shown in FIG. 5.

From the results, it can be understood that the intracellular accumulation of FDG and metabolism of that to FDG-6P decreased by the effect of glucose concentration in the medium but AFDG was substantially not affected by the glucose concentration. This means that FDG produced by hydrolysis of AFDG is metabolized to FDG-6P irrespective of the extracellular glucose concentration.

Example 4

Effect of Hexokinase Activity on Accumulation and Metabolism of FDG and AFDG

Figure 6:
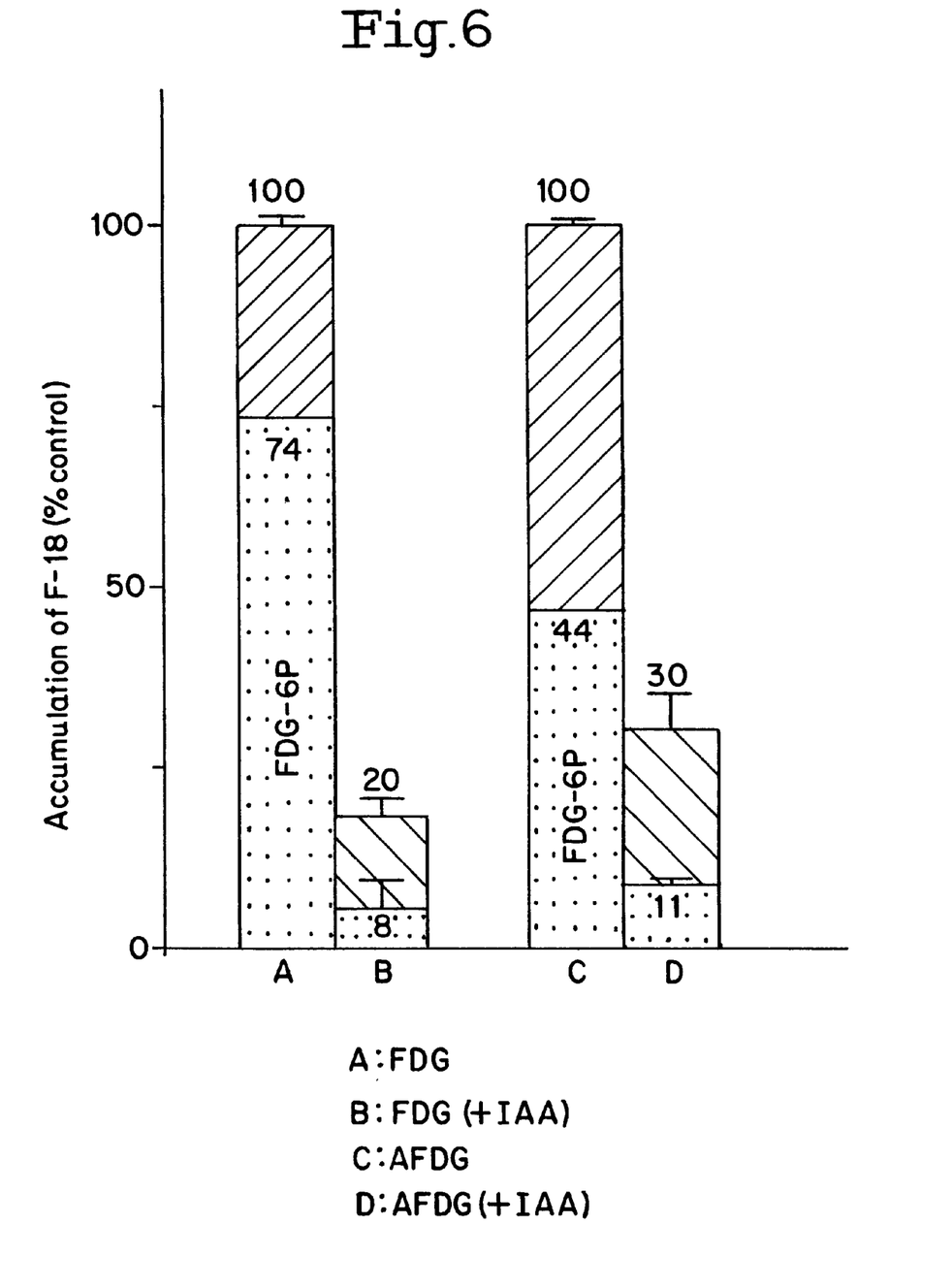
FIG. 6 shows the effect of iodoacetate (hereinafter referred to as IAA) on accumulation and metabolism of FDG and AFDG in LS180 cells.

Cells were added to a medium containing 5 µM IAA or 200 µM DNP, and simultaneously 5 µCi of FDG or 5 µCi of AFDG was added thereto and then cells were incubated at 37° C. Then, cells were washed three times with a cold PBS, lysed with 50% ethanol and assayed for metabolites. The results are shown in FIG. 6 and FIG. 7.

It can be understood that the intracellular accumulation of both of FDG and AFDG remarkably decreased in the presence of IAA, indicating that the rate-determining step in the metabolism of FDG and AFDG is phosphorylation by hexokinase. On the other hand, in the presence of DNP, while the accumulation of FDG increased, that of AFDG decreased. This is considered to be due to the facts that, while FDG is taken up with the aid of GLUT, AFDG is taken up without the aid of GLUT and that increase in expression of GLUT results in much amount of uptake of glucose, which compete against FDG formed by hydrolysis of AFDG and as the result FDG-6P derived from AFDG decreased.

What is claimed is:

1. A method for diagnosing pathological state of tumor cells, comprising the steps of administering an effective amount of a glucose derivative of the formula (I):

(I)

wherein $R^1$, $R^2$, $R^3$ and $R^4$ are the same or different and each represents a hydrogen atom or an acyl group having 2 to 8 carbon atoms, wherein at least one of $R^1$, $R^2$, $R^3$ and $R^4$ is an acyl group and $R^5$ is a radioisotope of a halogen atom, to the cells, which glucose derivative is hydrolyzed by esterase to produce 2-halodeoxyglucose, which 2-halodeoxyglucose is phosphorylated by hexokinase to produce a metabolite having a phosphorylated glucose derivative;

measuring the amount of the phosphorylated glucose derivative of the produced metabolites; and estimating hexokinase activity of the cells based on the amount of phosphorylated glucose derivative.

2. A method for diagnosing pathological state of tumor cells according to claim 1, wherein $R^5$ is a radioisotope of fluorine, and 2-halodeoxyglucose is 2-fluorodeoxyglucose.

3. A method for diagnosing pathological state of tumor cells according to claim 1, wherein $R^5$ is a radioisotope of bromine, and 2-halodeoxyglucose is 2-bromodeoxyglucose.

4. A method for diagnosing pathological state of tumor cells according to claim 1, wherein $R^5$ is a radioisotope of iodine, and 2-halodeoxyglucose is 2-iododeoxyglucose.

5. A method for diagnosing pathological state of tumor cells according to claim 1 or 2, wherein the glucose derivative is 1,3,4,6-tetra-O-acetyl-2-[F-18]fluorodeoxyglucose, and 2-halodeoxyglucose is 2-[F-18]fluorodeoxyglucose.

* * * * *